United States Patent [19]

Bönnemann et al.

[11] 4,266,061

[45] May 5, 1981

[54] PROCESS FOR PREPARATION OF 2-VINYLPYRIDINE FROM ACETYLENE AND ACRYLONITRILE

[75] Inventors: Helmut Bönnemann, Essen; Marc Samson, Hanau, both of Fed. Rep. of Germany

[73] Assignee: Studiengesellschaft Kohle mbH, Mulheim, Fed. Rep. of Germany

[21] Appl. No.: 75,458

[22] Filed: Sep. 14, 1979

[30] Foreign Application Priority Data

Sep. 16, 1978 [DE] Fed. Rep. of Germany ....... 2840460

[51] Int. Cl.³ .............................................. C07D 213/12
[52] U.S. Cl. .................... 546/253; 546/350; 546/352; 546/4; 252/413; 260/439 R; 260/439 CY
[58] Field of Search ................... 546/253, 350, 352

[56] References Cited

U.S. PATENT DOCUMENTS

| 3,829,429 | 8/1974 | Clement | 546/253 |
| 4,006,149 | 2/1977 | Bonnemann et al. | 546/253 |
| 4,212,978 | 7/1980 | Hardt | 546/253 |

OTHER PUBLICATIONS

Wakatsuki et al. "Synthesis", (1976) No. 1, pp. 26-28.

*Primary Examiner*—Robert T. Bond
*Attorney, Agent, or Firm*—Sprung, Felfe, Horn, Lynch & Kramer

[57] ABSTRACT

A process is described for the catalytic, selective preparation of 2-vinylpyridine from acetylene and acrylonitrile using a cyclopentadienylcobalt catalyst or π-allylcobalt catalyst at elevated temperature in an inert solvent, wherein the acrylonitrile concentration is up to 2 mols/liter and the reaction is carried out at a temperature over 140° C. and up to 180° C., the reaction time being not more than 50 minutes.

9 Claims, No Drawings

PROCESS FOR PREPARATION OF 2-VINYLPYRIDINE FROM ACETYLENE AND ACRYLONITRILE

BACKGROUND OF THE INVENTION

1. Field of the Invention

This invention relates to a process for the selective preparation of 2-vinylpyridine from acetylene and acrylonitrile with a soluble organocobalt catalyst. As a result of the invention, one can convert acetylene and acrylonitrile selectively, with only moderate catalyst usage, into 2-vinylpyridine.

2. Discussion of the Prior Art

The processes to date for vinylpyridine synthesis are economically unsatisfactory with respect to catalyst utilization and product yields, as is apparent from the data presented in Table 1 which follows.

TABLE 1

| Literature | Catalyst | Temp. °C. | Nitrile concentration mols/l | Residence time min. | Pyridine yield based on acrylonitrile conversion | Turn over Number Mol 2-vinylpyridine/ g-atom Co |
|---|---|---|---|---|---|---|
| DOS 26 153 09 P. Hardt Lonza AG Example 3 | Cobaltocene | 120 | 4.57 | 60 | 41.6% | 38 |
| H. Yamazaki, J. Wakatsuki Synthesis 1976, 26, page 28 | Cobaltocene | 110 | 5.05 | 420 | 31.0% | 48.0 |
| U.S. Pat. No. 4,006,149 Studienges. Kohle mbH Example 40 | Cyclopentadienylcobalt cyclooctadiene | 100 | 2.144 | 240 | 75.0% | 63.0 |

Yamazaki et al. obtained a 2-vinylpyridine yield of 31% using cobaltocene as catalyst. The synthesis was carried out at 110° C. with a reaction time of 7 hours and an acrylonitrile concentration of 5.05 mols/liter. The reaction was deliberately carried out at a considerably lower temperature, i.e., 110° C., than those employed in the production of other pyridine derivatives in order to reduce the loss of vinylpyridine due to polymerization. According to P. Hardt, a reduction of the reaction time to 60 minutes, using the same catalyst, a slightly higher temperature (120° C.) and a slightly lower nitrile concentration (4.57 mols/l), failed to produce the desired results. The yield was under 45%, which is too low to make the process economically worthwhile.

U.S. Pat. No. 4,006,149, the disclosure of which is hereby specifically incorporated herein by reference, names cobalt (I) complex compounds as catalysts, also for the preparation of vinylpyridines. These catalysts are considerably more effective than cobaltocene, the catalyst of the aforesaid disclosures. At 100° C. and with a residence time of 4 hours and a nitrile concentration of 2.14 mols/l, a yield of 75% is obtained. With the parameters selected as above, a lower nitrile concentration and a moderately long reaction time, it was not likely that a substantial improvement in the result of the synthesis could be obtained by the use of cobaltocene, for example, as catalyst.

Surprisingly, and contrary to all experience, it has now been found that the yield of 2-vinylpyridine susceptible to polymerization can be drastically increased when the temperature is raised to 150° C. and above, the residence time is reduced to less than 50 minutes, and the nitrile concentration is selected at under 2 mols/l. Suitable catalysts for this selective synthesis of 2-vinylpyridine then are cyclopentadienylcobalt compounds or π-allylcobalt compounds generally.

The catalysts are employed in an amount between 0.05–0.5 mol %, preferably 0.1 to 0.3 mol %, based on mols acrylnitrile charged.

With regard to selection of the temperature, the range around 150° to 160° C. is advantageous; however, temperatures ranging from 140° to 180° C. may also be used.

The reaction time may range from about 5 minutes to not more than 50 minutes; however, it may also be under 5 minutes and as short as a few seconds when suitable reaction apparatuses such as flow pipes are used. As a rule, a reaction time between 15 and 30 minutes will be advantageous.

The acrylonitrile concentration may range from about 0.1 mol/l to 2 mols/l or higher. The acrylonitrile concentration is preferably about or above 1 mol/l. The mol ratio of acetylene to acrylnitrile is generally 0.5 to 2:1, preferably 1 to 1.5:1.

Suitable solvents are those which are inert to the reactants over the temperature range specified. Such solvents are aliphatic solvents, for example, and particularly aromatic solvents such as benzene or toluene. Useful aliphatic solvents include: pentane, hexane, commercially available aliphatic mixtures.

The reaction in accordance with the invention is preferably carried out in a pressure vessel equipped with efficient mixing means to provide assurance that the solution is saturated with acetylene during the reaction. The acetylene pressure may range from 5 to 20 atm and is preferably comprised between 8 and 17 atm.

Suitable catalysts for the process in accordance with the invention are temperature-resistant cobalt compounds containing at least one cyclopentadienyl bound to the cobalt, such as bis-cyclopentadienylcobalt (cobaltocene), cyclopentadienylcobalt cyclooctadienee or cyclopentadienylcobalt dicarbonyl, for example. π-allylcobalt compounds can also be used, such as methyl-heptadienylbutadiene-cobalt, cyclooctenylcyclooctadiene(1,5)-cobalt. Useful catalysts of the above type include all those described or named in U.S. Pat. No. 4,006,149, supra.

The process may be carried out discontinuously or, optionally, continuously, either in cascaded agitator vessels or in a flow pipe, it being important to provide for rapid cooling of the effluent stream. The catalyst is advantageously used in the form of prefabricated cobalt compounds. However, it may also be prepared in situ in the reaction mixture.

The 2-vinylpyridine prepared in accordance with the invention finds use as a component of terpolymeric adhesion promoters in the manufacture of tires and also serves as a comonomer in the production of acrylic fibers.

In order to more fully illustrate the invention and the manner of practicing the same, the following examples are presented.

In the examples when catalysts utilization is given, "pyridine" means "2-vinylpyridine". Catalyst utilization is expressed in "mols pyridine per g-atom cobalt".

EXAMPLE 1

0.12 g (0.52 millimole) cyclopentadienylcobalt cycloocta-(1,5)-diene is dissolved in 241.6 ml toluene and mixed with 14.05 g (264.8 millimoles) acrylonitrile solution including the catalyst. This solution is drawn at 20° C. into a 500-ml high-grade steel autoclave having magnetic agitating means. The solution is saturated with acetylene at 7 bars and heated within 15 min to 150° C., the pressure being raised to 17 to 18 atm by injecting acetylene. The acetylene consumed is replaced continuously. After a residence time of 30 min at 150° C., the temperature in the pressure vessel is reduced within 10 min to 30° C. through external cooling.

233 g of crude product is discharged from the autoclave, and the volatile constituents are condensed off at 0.2 mm Hg, there remaining 1.90 g of residue. Gas-chromatographic analysis shows the condensate to contain 8.13 g acrylonitrile and 10.88 g 2-vinylpyridine.

| Yield, based on | |
|---|---|
| reacted acrylonitrile: | 93% 2-vinylpyridine |
| Catalyst utilization: | 200 mols pyridine/g at cobalt |

EXAMPLE 2

The procedure described in Example 1 is followed, except that cobaltocene is used as catalyst.

Charged:
| 0.2 g | (1.06 mMol) | cobaltocene | |
|---|---|---|---|
| 13.05 g | (246 mMol) | acrylonitrile | } 0.95-molar solution |
| 209.9 g | (242 ml) | toluene | |

Conditions: Reaction temperature: 148° C.
Residence time at 148° C.: 50 min.
Reaction product: 231.20 g
Condensate (0.2 mm Hg): 227.70 g
Residue: 3.05 g
Result (based on gas-chromatographic analysis):
 6.25 g unreacted acrylonitrile
 10.44 g 2-vinylpyridine
Yield, based on
 reacted acrylonitrile: 78% 2-vinylpyridine
Catalyst utilization: 94 mols pyridine/g at cobalt

EXAMPLE 3

The procedure described in Example 1 is followed, except that π-cyclopentadienyldicarbonylcobalt is used as catalyst.

Charged:
| 0.135 g (0.86 millimol) | π-C$_5$H$_5$Co(CO)$_2$ | |
|---|---|---|
| 20.7 g (390.6 millimols) | acrylonitrile | } 1.50-molar solution |
| 203.5 g (234 ml) | toluene | |

Conditions: Reaction temperature: 155° C.
Residence time at 155° C.: 30 min.
Reaction product: 229.5 g
Condensate (0.2 mm Hg): 228.3 g
Residue: 0.7 g
Result (based on gas-chromatographic analysis):
 15.12 g unreacted acrylonitrile
 8.89 g 2-vinylpyridine
Yield, based on
 reacted acrylonitrile: 80.4% 2-vinylpyridine
Catalyst utilization: 98 mols pyridine/g at cobalt

EXAMPLE 4

The procedure described in Example 1 is followed, except that π-cyclopentadienyl-(1-exo-trichloromethylcyclopentadiene)cobalt is used as catalyst.

Charged:
| 0.245 g (0.797 millimol) | π-C$_5$H$_5$CoC$_5$H$_5$CCl$_3$ | |
|---|---|---|
| 13.65 g (257.6 millimols) | acrylonitrile | } 1.02-molar solution |
| 206.4 g (237 ml) | toluene | |

Conditions: Reaction temperature: 150° C.
Residence time at 150° C.: 30 min.
Reaction product: 223.6 g
Condensate (0.2 mm Hg): 222.8 g
Residue: 0.6 g
Result (based on gas-chromatographic analysis):
 9.73 g unreacted acrylonitrile
 6.37 g 2-vinylpyridine
Yield, based on
 reacted acrylonitrile: 82% 2-vinylpyridine
Catalyst utilization: 76 mols pyridine/g at cobalt

EXAMPLE 5

The procedure described in Example 1 is followed, except that π-cyclopentadienyl-(1-exo-cyanomethylenecyclopentadiene)cobalt is used as catalyst.

Charged:
| 0.206 g (0.897 millimols) | π-C$_5$H$_5$CoC$_5$H$_5$CH$_2$CN | |
|---|---|---|
| 16.25 g (306.6 millimols) | acrylonitrile | } 1.17-molar sol'n |
| 209.6 g (241 ml) | toluene | |

Conditions: Reaction temperature: 155° C.
Residence time at 155° C.: 30 min.
Reaction product: 236.75 g
Condensate (0.2 mm Hg): 232.6 g
Residue: 4.0 g
Result (based on gas-chromatographic analysis):
 7.27 g unreacted acrylonitrile
 13.74 g 2-vinylpyridine
Yield, based on
 reacted acrylonitrile: 77% 2-vinylpyridine -continued

| | |
|---|---|
| Catalyst utilization: | 146 mols pyridine/g at cobalt |

EXAMPLE 6

0.2 g (0.9 millimol) methylheptadienyl-butadienecobalt is dissolved at −30° C. in 233 ml toluene and mixed with 0.05 g (0.94 millimol) monomeric cyclopentadiene. The mixture is heated to 20° C. and 19.2 g (362.3 millimols) acrylonitrile is added to give a 1.41-molar solution of acrylonitrile in toluene. Apart from this, the procedure followed is the same as that described in Example 1.

| Conditions: | Reaction temperature: | 155° C. |
|---|---|---|
| | Residence time at 155° C. | 30 min. |
| Reaction product: | 227.9 g | |
| Condensate (0.2 mm Hg): | 225.8 g | |
| Residue: | 1.85 g | |
| Result (based on gas-chromatographic analysis): | | |
| 12.69 g unreacted acrylonitrile | | |
| 9.74 g 2-vinylpyridine | | |
| Yield, based on | | |
| reacted acrylonitrile: | 75.3% 2-vinylpyridine | |
| Catalyst utilization: | 103 mols pyridine/g at cobalt | |

EXAMPLE 7

The procedure described in Example 1 is followed, except that π-indenylcyclooctadiene-1,5-cobalt is used as catalyst.

| Charged: | | |
|---|---|---|
| 0.1492 g | (0.529 millimol) | indenylcobalt-COD* |
| 26.20 g | (494.3 millimols) | acrylonitrile (1.65-molar) |
| 231.25 g | | toluene |
| Conditions: | Reaction temperature: | 140° C. |
| | Residence time at 140° C. | 20 min. |
| Reaction product: | 271.15 g | |
| Condensate (0.2 mm Hg): | 268.3 g | |
| Residue: | 2.6 g | |
| Result (based on gas-chromatographic analysis): | | |
| 16.79 g unreacted acrylonitrile | | |
| 16.44 g 2-vinylpyridine | | |
| Yield, based on | | |
| reacted acrylonitrile: | 88% 2-vinylpyridine | |
| Catalyst utilization: | 294 mols pyridine/g at cobalt | |

EXAMPLE 8

101.4 mg (0.3595 millimol) π-indenylcobalt-COD is dissolved in 151.8 g toluene and mixed with 19.0 g (358.5 millimols) acrylonitrile to give 200 ml of a 1.79-molar nitrile solution, including the catalyst. This solution is introduced at 20° C. into a 500-ml high-grade steel autoclave. The solution is then saturated with acetylene at 7 bars. The temperature is then raised to 145° C. over a period of 12 min, the pressure being increased to 18.5 bars by injection of acetylene and then held constant.

After a reaction time of 17 min, 105.5 mg (0.374 millimol) indenylcobalt-COD, dissolved in 29.9 g toluene, is metered in over a period of 6 min. After a reaction time of 18 min at 145° C., the pressure vessel is cooled down to 25° C. within 10 min.

| | |
|---|---|
| Reaction time: | 41 min |
| Reaction temperature: | 145° C. |

-continued

| | |
|---|---|
| Reaction product: | 210.7 g |
| Condensate (0.2 mm Hg): | 206.6 g |
| Residue: | 2.9 g |
| Result (based on gas-chromatographic analysis): | |
| 9.31 g unreacted acrylonitrile | |
| 15.4 g 2-vinylpyridine | |
| Yield, based on | |
| reacted acrylonitrile: | 79% 2-vinylpyridine |
| Catalyst utilization: | 197 mols pyridine/g at cobalt |

EXAMPLE 9

Preparation of 2-vinylpyridine by the use of trimethylsilylpentadienyl (cycloocta-1,5-diene)cobalt as catalyst

| Charged: | | | |
|---|---|---|---|
| 0.222 g | (0.730 millimol) | Me₃SiCpCoCOD | |
| 15.55 g | (293.40 millimols) | acrylonitrile | (1.13-molar) |
| 208.65 g | toluene | | |
| Conditions: | Reaction temperature: | 150° C. | |
| | Reaction time: | 30 min | |
| Reaction product: | 233.55 g | | |
| Condensate (0.2 mm Hg): | 231 g | | |
| Residue: | 2.0 g | | |
| Result (based on gas-chromatographic analysis): | | | |
| 9.51 g acrylonitrile (unreacted) | | | |
| 10.94 g 2-vinylpyridine | | | |
| Yield, based on | | | |
| reacted acrylonitrile: | 91% 2-vinylpyridine | | |
| Catalyst utilization: | 143 mols pyridine/g at cobalt | | |

EXAMPLE 10

Preparation of 2-vinylpyridine by the use of π-cyclopentadienyl (α,α'-bipyridil)cobalt as catalyst

| Charged: | | | |
|---|---|---|---|
| 0.150 g | (0.536 millimol) | CpCobipy | |
| 16.70 g | (315.1 millimols) | acrylonitrile (1.21-molar) | |
| 209.25 g | | toluene | |
| Conditions: | Reactuon temperature: | 145° C. | |
| | Reaction time: | 15 min | |
| Reaction product: | 233.50 g | | |
| Condensate (0.2 mm Hg): | 229.80 g | | |
| Residue: | 1.5 g | | |
| Result (based on gas-chromatographic analysis): | | | |
| 10.55 g acrylonitrile (unreacted) | | | |
| 9.82 g 2-vinylpyridine | | | |
| Yield, based on | | | |
| reacted acrylonitrile: | 81% 2-vinylpyridine | | |
| Catalyst utilization: | 174 mols pyridine/g at cobalt | | |

Preparation of π-indenyl(cycloocta-1,5-diene)cobalt

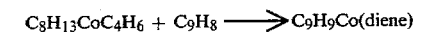

(222)            (116)

Natta complex   Indene

(108)            (284)

Ind Co COD 3.8 g (17.1 millimols) Natta complex, dissolved in 100 ml pentane, is mixed with 1.98 g (17.1 millimols) indene at −30° C. The reaction solution is then slowly brought to room temperature and the reaction is allowed to proceed for 20 h. About 5 ml COD-1,5 is then added. The clear red solution is heated to reflux for about 24 h. After cooling, the precipitate, if any, is filtered off and the solution is concentrated to about 30 ml and slowly cooled down to −50° C. Brown-red crystals then form. The supernatant mother liquor is then squeezed off and the crystals (needles of a red-brown color) are dried for 1 h at reaction temperature in a high vacuum (10⁻⁴ mm Hg).

Yield: 2.4 g (50% of theory)
Melting point: 98° C.
Elementary analysis: Found: C: 73.20%; H: 6.86%; Co: 19.29%: Calculated: C: 72.34%; H: 6.78%; Co: 20.88%.
IR analysis: 1450, 1325, 1315, 1200, 1030, 960, 905, 840, 790, 735, 725 cm⁻¹
¹H NMR (d₈ toluene, 80 MHz):

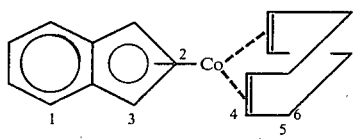

δH₁: 7.14 (s)
δH₂: 5.78 (t, J=2.4 Hz)
δH₃: 3.89 (d, J=2.4 Hz)
δH₄: 3.40 (m)
δH₅: 2.09 (m)
δH₆: 1.40 (m)
¹³C NMR (d₈ toluene:

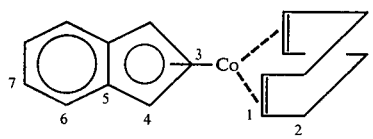

δC₁: 67.38 (d, J$_{C,H}$=152 Hz)
δC₂: 31.35 (t, J$_{C,H}$=127 Hz)
δC₃: 88.51 (d, J$_{C,H}$=174.6 Hz)
δC₄: 75.80 (d, J$_{C,H}$=174.4 Hz)
δC₅: 105.48 (s)
δC₆: 124.27 (d, J$_{C,H}$=159 Hz)
δC₇: 122.98 (d, J$_{C,H}$=161 Hz)
Mass spectrum: m/e: 282 (M⁺; 100%), 252 (42%), 174 (80%), 164 (25%), 138 (28%), 124 (30%), 115 (45%), 59 (15%).
Literature: "π-indenyl(cyclooctatriene)cobalt", A. Greco, M/Green, F. G. Stone, J. Chem. Soc. (A), 286 (1971)

Preparation of π-trimethylsilylcyclopentadienyl(cycloocta-1,5-diene)cobalt

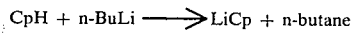

(66)

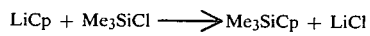

(72)  (108.5)  (138)

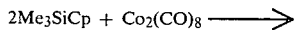

(138)  (342)

-continued
Preparation of π-trimethylsilylcyclopentadienyl(cycloocta-1,5-diene)cobalt

(252)

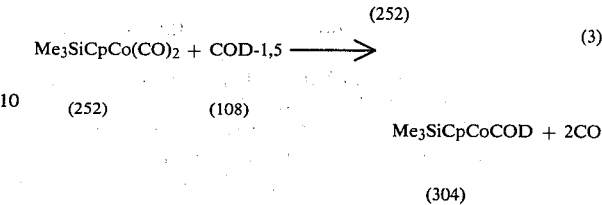

(1) 33 g (0.5 mol) cyclopentadiene is charged at room temperature and diluted with 200 ml benzene and 100 ml tetrahydrofuran. Over a period of 2 h, 213 ml of a 15% solution of butyllithium in hexane is added dropwise. 64.5 g (0.5 mol) trimethylsilyl chloride, dissolved in 100 ml benzene, is then added dropwise and the reaction mixture is boiled for 15 h with refluxing. After cooling, the white precipitate formed (LiCl) is filtered off and washed with benzene. The filtrate is concentrated and then distilled.
Boiling point: 60° to 65° C./Water-jet vacuum pump about 10 mm Hg.
Yield: 30 g (46.5% of theory).
(2) About 10 ml trimethylsilylcyclopentadiene is added to a solution of 3.42 g (10 millimols) Co₂(CO)₈ in 20 ml ether. The mixture is heated for 1 h to reflux. After filtration, the solvent is decanted and the residue is distilled.
Boiling point: 50° to 52° C./0.5 mm Hg.
Yield: 4.3 g (85% of theory).
(3) A solution of 3.90 g (14.8 millimols) Me₃SiCp-(CO)₂ in 10 ml COD-1,5 is heated to reflux over a period of 12 h. After cooling, the solution is concentrated and a light-brown crystalline mass is obtained as residue. Recrystallization from pentane at −40° C. then yields the pure product.
Yield: 3.6 g (80% of theory).
Melting point: 64° C.
Elementary analysis: Found: C: 64.54%, H: 7.98%, Co: 18.53%, Si: 8.82%; Calculated: C: 63.16%, H: 8.55%, Co: 19.41%, Si: 9.04%.
IR analysis:
1440, 1360, 1315, 1240, 1155, 1055, 1040, 900, 875, 850, 820 (s), 800, 740, 680, 620 cm⁻¹.
¹H NMR (d₈ toluene, 60 MHz):

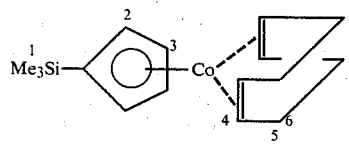

δH₁: 0.0 (s), internal standard
δH₂: 3.0 (t, J=2 Hz)
δH₃: 4.38 (t, J=2 Hz)
δH₄: 1.22 (m)
δH₅: 2.0 (m)
δH₆: 3.0 (m)
Mass spectrum: m/e: 304 (M⁺; 45%), 229 (100%), 196 (40%), 181 (18%), 137 (15%), 124 (15%), 107 (20%), 93 (10%), 73 (18%)

Literature:

1. Preparation of Me₃SiCpH: K. C. Frisch, J. Am. Chem. Soc. 75, 6050 (1953).
2. Preparation of Me₃SiCpCo(CO)₂: E. W. Abel, S. Moorhouse, J. Organomet. Chem. 28, 211–215 (1971).
3. General literature on SiCp-metal compounds: "Advances in Organometallic Chemistry", vol. 15 (1977), I. Haidue, V. Popa, p. 113 (Academic Press).

Preparation of π-cyclopentadienyl-α,α'-bipyridylcobalt

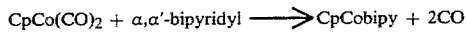

(180)    (156)    (280)

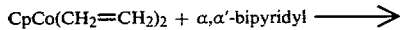

(180)    (156)

CpCobipy + 2CH₂=CH₂

(280)

(1) A solution of 7.06 g (45.3 millimols) α,α'-bipyridyl in 50 ml xylene is added dropwise at room temperature to a solution of 8.15 g (45.3 millimols) cyclopentadienylcobalt dicarbonyl in 100 ml xylene. The solution is then heated to reflux. The progress of the reaction may be gauged by the fact that decreasing amounts of CpCo(CO)₂ are entrained by the solvent until the reflux finally condenses colorless. The reaction time at 160° C. is about 12 h. During the reaction the color changes from a deep red to a deep violet. After cooling and concentration of the solvent, a black-violet precipitate is obtained which is recrystallized from pentane at −50° C.

Yield: 10.7 g (84% of theory)

Elementary analysis: Found: C: 64.01%, H: 5.6%, N: 10.03%, Co: 20.90%: Calculated: C: 64.30%, H: 4.68%, N: 10.00%, Co: 21.03%.

Mass spectrum:

m/e 280 (M⁺; 100%), 215 (89%), 189 (10%), 162 (10%), 156 (29%), 140 (14%), 130 (14%), 59 (20%).

We claim:

1. In a process for the catalytic, selective preparation of 2-vinylpyridine from acetylene and acrylonitrile employing a cyclopentadienylcobalt catalyst or π-allylcobalt catalyst at an elevated temperature in an inert solvent, the improvement wherein mol ratio of actylene to acrylonitrile is generally 0,5 to 2:1 and the reaction is carried out at a temperature of over 140° C. and up to 180° C., the reaction time being not more than 50 minutes.

2. A process according to claim 1 wherein the temperature ranges from 150° to 160° C.

3. A process according to claim 1 wherein the reaction time ranges from 15 to 30 minutes.

4. A process according to claim 1 wherein the acrylonitrile concentration is about 1 mol/liter.

5. A process according to claim 1 wherein cobaltocene is used as catalyst.

6. A process according to claim 1 wherein the catalyst is prepared in situ.

7. A process according to claim 1 wherein the catalyst is π-indenyl(cycloocta-1,5-diene)cobalt.

8. A process according to claim 1 wherein the catalyst is π-trimethylsilylcyclopentadienyl(cycloocta-1,5-diene)cobalt.

9. A process according to claim 1 wherein the catalyst is π-cyclopentadienyl-α,α'-bipyridylcobalt.

* * * * *